(12) United States Patent
Ericson (10) Patent No.: US 8,043,826 B2
(45) Date of Patent: Oct. 25, 2011

(54) DEVICE FOR MONITORING INHIBITION OF PLATELET FUNCTION RESPONSE

(75) Inventor: Daniel G. Ericson, Rochester, MN (US)

(73) Assignee: Medical Innovations International, Inc., Rochester, MN (US)

( * ) Notice: Subject to any disclaimer, the term of this patent is extended or adjusted under 35 U.S.C. 154(b) by 734 days.

(21) Appl. No.: 11/632,780

(22) PCT Filed: May 14, 2005

(86) PCT No.: PCT/US2005/016882
§ 371 (c)(1),
(2), (4) Date: Apr. 28, 2008

(87) PCT Pub. No.: WO2005/113800
PCT Pub. Date: Dec. 1, 2005

(65) Prior Publication Data
US 2008/0254491 A1    Oct. 16, 2008

(51) Int. Cl.
*C12Q 1/66* (2006.01)
*C12M 1/34* (2006.01)

(52) U.S. Cl. ......... 435/8; 435/288.7; 435/288.2; 436/63

(58) Field of Classification Search ........... 435/8, 288.7, 435/288.2; 436/63
See application file for complete search history.

(56) References Cited

U.S. PATENT DOCUMENTS
6,716,391 B1    4/2004 Olson

FOREIGN PATENT DOCUMENTS
EP          05772254        10/2008
WO          WO 0117649       3/2001
WO          WO2005113800    12/2005

OTHER PUBLICATIONS

Scazziota et al. ,Thrombosis Research 100 479-488 (2000).*
Abraham, E.H., et al., "Erythrocyte membrane ATP' binding cassette (ABC) proteins: MRP1 and CFTR as well as CD39 (ectopyrase) involved in RBC AT", "Blood Cells Molecules and Diseases", 2001, pp. 165-180, vol. 27.
Accumetrics (Company), "VerifyNow Asprin Assay", "web address: http://www.accumetrics.com/products/ultegra_asa.html.", 1996, Publisher: Accumetrics.
Altman, R., et al., "The antithrombotic profile of aspirin. Aspirin resistance, or simply failure?", "Thrombosis J.", 2004, pp. 1-8, vol. 2.
Bhatt, D.L., et al., "Aspirin resistance: more than just a laboratory curiosity", "J. Am. College of Cardiology", 2004, vol. 43, No. 6.
Biocarta (Company), "Pathways: Asprin Blocks Signaling Pathway Involved in Platelet Application", "Charting Pathways of Life http://www.biocarta.com/pathfiles/h_sppaPathway.asp.", 2004.
Bolla, M., et al., "Cyclooxygenase involvement in thromboxane-dependent . . . ", "Hypertension", 2004, pp. 1264-1269 , vol. 43.
Born, G.V.R., "Aggregation of Blood Platelets by Adenosine Diphosphate and Its Reversal", "Nature", Jun. 9, 1962, pp. 927-929, vol. 194, No. 4832.
Chen, W.H., et al., "Aspirin resistance is associated with a high incidence of myonecrosis . . . ", "J. Am. Coll. Cardiol.", 2004, pp. 1127-1129, vol. 43.
Cho, et al., "The roles of LAT in platelet signaling induced by collagen, TxA2, or ADP", "Biochem Biophys Res Comm", 2002, pp. 916-921, vol. 292.
De Gaetano, G., et al., "Aspirin resistance: a revival of platelet aggregation tests?", "J. Thrombosis and Haemostasis", 2003, pp. 2048-201, vol. 1.
Gum, P.A., et al., "Profile and prevalance of aspirin resistance in patients with cardiovascular disease", "Am. J. Cardiology", 2001, p. 230, vol. 88.
Knoffler, et al., "Critical evaluation of the quantification of ATP release reaction in whole blood", "Thrombosis Res", 1996, pp. 157-165, vol. 84, No. 3.
Miller, Jonathan L., "Platelet Function Testing: An Improved Approach Utilizing Lumi-aggregation and an Interactive Computer System", "Division of Clinical Pathology, State University of New York, Upstate Medical Center, Syracuse, New York", Apr. 1984, pp. 471-476, vol. 81, No. 4.
Puri, "Phospholipase A2: its role in ADP- and thrombin-induced platelet activation mechanisms", "Int J Biochem Cell Biol", 1998, pp. 1107-1122, vol. 30.
Rodgers, G.M., "Overview of platelet physiology and laboratory evaluation of platelet function", "Clin. Obstet. Gynecol", 1999, pp. 349-359, vol. 42.
Scazziota, et al., "Abciximab treatment in vitro after aspirin treatment in vivo has additive effects on platelet aggregation, ATP release,", "Thrombosis Res", 2000, pp. 479-488, vol. 100.
Steinhubl, et al., "Point-of-care measured platelet inhibition correlates . . . ", "Circulation", , pp. 2572-2578, vol. 103, (2001).
Stiene-Martin, et al., "The Megakaryocyte-Platelet System", "Clinical Hematology: Principles, Procedures, Correlations", 1998, vol. 2.
Taylor, et al., "The differential effect of aspirin on human platelet activation in aspirin-sensitive asthmatics and normal subjects", "British J. Clin. Pharmacology", 1993, pp. 227-234, vol. 35.
Vane, J.R., et al., "The mechanism of action of aspirin.", "Thrombosis Research", 2003, pp. 255-258, vol. 110.
Wu, K.K. et al., "Monitoring platelet function in glycoprotein IIb/IIIa inhibitor therapy", "Circulation", , pp. 2528-2530, vol. 103, (2001).

* cited by examiner

*Primary Examiner* — Chih-Min Kam
(74) *Attorney, Agent, or Firm* — Charles A. Lemaire; David J. King; Lemaire Patent Law Firm, P.L.L.C.

(57) ABSTRACT

The invention provides a method of monitoring the response of platelets to a COX1 inhibitor such as aspirin. The method involves collecting platelet-containing mammalian blood treated with a COX 1 inhibitor; mixing the blood with a COX 1-dependent platelet agonist, such as arachidonic acid, monitoring extracellular ATP in the agonist-activated blood to generate a measurement, and comparing the measurement to a standard value. Devices, systems, and kits for carrying out the method are also provided.

40 Claims, 7 Drawing Sheets

DEVICE FOR MONITORING INHIBITION OF PLATELET FUNCTION RESPONSE

This application is a U.S. National Phase Entry of PCT/US2005/016882, which was filed May 14, 2005. This application also claims priority from U.S. patent application Ser. No. 10/846,439, filed May 14, 2004 (now abandoned), titled "Method and device for monitoring inhibition of platelet function."

BACKGROUND

Millions of people are taking aspirin as therapy to reduce the risk of heart attacks and other cardiovascular events. These include persons with elevated cholesterol, a family history of heart disease, or other risk factors for cardiovascular disease. Among those with risk factors, nearly all persons with implanted cardiovascular devices are at elevated risk of clot formation and embolization and are prescribed some anti-platelet agent, usually aspirin. In addition, many healthy people without a recognized elevated risk of cardiovascular disease also take aspirin as a precaution.

Platelets function to stop bleeding by forming clots, and they initiate the process of wound healing. This occurs when platelets are activated, causing them to change shape, adhere, spread, release chemical messengers and activators, aggregate, and assemble with fibrin.

But platelet activation and clot formation can also place a person at risk of pathological cardiovascular events. For example, venous blood clot formation in the legs, a condition known as deep vein thrombosis, creates the risk that the blood clots could embolize (break apart) and result in clot entrapment in the lungs or the brain, causing pulmonary embolisms and stroke-related conditions. Platelet activation and fibrin formation in other locations in some persons create aggregates and small clots in the arterial circulation that can also lead to embolization and strokes.

Each year, approximately 500,000 heart valves are implanted in the United States. Although biomaterial advancement has somewhat reduced the risk of thrombosis (clot formation), all patients with mechanical heart valves are at increased risk of clot formation, embolization, and stroke, and are usually placed on aspirin therapy.

Arterial stents are another type of device placed in the circulatory system that place patients at risk from platelet activation. Arterial stents are placed in clogged coronary and carotid arteries to provide oxygen to cardiac tissue. They are typically around 5 mm in diameter and are made from stainless steel or other materials. Due to the introduction of a foreign material in the blood stream, platelets can become activated and attach to the wall of the stented vessel. This leads to reocclusion (restenosis) of the stented vessel, which is a very significant risk in patients with arterial stents. Restenosis in the first 28 days is reported in 0.5 to 8% of persons receiving stents.

To reduce these and other risks of cardiovascular pathology, millions of patients are placed on anti-platelet drugs, most commonly aspirin.

It is useful here to briefly summarize the biochemical events of hemostasis (the cessation of bleeding) and aspirin's role in inhibiting the process. Normal intact vascular endothelium does not initiate or support platelet adhesion (although in certain vascular diseases platelets may adhere to intact endothelium). Vascular injury, however, exposes the endothelial surface and underlying collagen. Following vascular injury, platelets attach to adhesive proteins such as collagen via specific glycoproteins on the platelet surface. This adhesion is followed or accompanied by platelet activation, where platelets undergo a shape change from a disc shape to a spherical shape with extended pseudopodia. At this time, the platelet release reaction also occurs. The platelets release biologically active compounds stored in the cytoplasmic bodies that stimulate platelet activation or are otherwise involved in clotting reactions. These include ADP, serotonin, thromboxane $A_2$, and von Willebrand factor.

Following activation, glycoprotein receptors on the surface of the platelets undergo a conformational change from a relatively inactive conformation to an activated form. The activated receptors mediate the adhesion of more platelets by adhering to the circulating plasma protein fibrinogen, which serves as a bridging ligand between platelets. The adhesion and aggregation of platelets constitutes primary hemostasis.

Secondary hemostasis stabilizes the platelet mass by forming a fibrin clot. The fibrin clot is the end product of a series of reactions involving plasma proteins. The process is known as blood coagulation. In coagulation, fibrin is formed from fibrinogen, a large circulating plasma protein, by specific proteolysis. In the process, the protein thrombin is consumed. Fibrin monomers next spontaneously associate to form polymers and form a loose reinforcement of the platelet plug. Fibrin polymers are then cross-linked by certain enzymes. The fibrin polymer also traps red cells and white cells to form a finished clot.

Platelets are activated by a variety of stimuli. Collagen, ADP, thrombin, and physical shear stress all activate platelets. One of the first steps in activation is that a platelet membrane phospholipase, phospholipase $A_2$, cleaves membrane lipids to release the fatty acid arachidonic acid. Arachidonic acid is oxidized in the platelet by the enzyme cyclooxygenase to the prostaglandin $PGG_2$. $PGG_2$ can be enzymatically converted to $PGH_2$, and $PGH_2$ is converted by thromboxane synthetase to thromboxane $A_2$ ($TxA_2$).

$TxA_2$ is a very potent activator of platelets and greatly amplifies the platelet release reaction, where the platelets secrete the contents of certain cytoplasmic bodies, including alpha granules and dense bodies. Among the components secreted from dense bodies are ADP, $Ca^{++}$, $Mg^{++}$, and serotonin.

Aspirin acts by acetylating and inactivating cyclooxygenase-1 in platelets, preventing the synthesis of $TxA_2$. By preventing the synthesis of $TxA_2$, aspirin significantly reduces platelet activation and thus reduces clotting. Aspirin inactivates cyclooxygenase-1 (COX1) at a lower dose and more completely than it inactivates or inhibits another isoform of cyclooxygenase, cyclooxygenase-2. COX1 is the predominant cyclooxygenase in platelets. COX2 is involved in inflammation. (Vane, J. R., et al., 2003, The mechanism of action of aspirin, *Thrombosis Research* 110: 255.)

Thus, by inhibiting platelet activation, aspirin for most patients is an effective agent to prevent clots and pathological cardiovascular events. But many people are resistant to aspirin. In one study, 5.5% or 9.5% of patients were resistant to aspirin, as assayed by two different techniques, and 23.8% of patients were semi-resistant (Gum, P. A., et al., 2001, *Am. J Cardiology* 88: 230). Other studies estimate 5-40% of patients are aspirin resistant, depending on the assay and the population studied (Bhatt, D. L., 2004, *J. Am. College of Cardiology* Vol. 43, No. 6, 2004). This is very important, because aspirin resistance is significantly associated with an increased risk of death, myocardial infarction, or cerebrovascular accident (Altman, R., et al., 2004, *Thrombosis J.* 2: 1).

It is important to identify patients resistant to aspirin or other COX1 inhibitors, because if they are identified they can be placed on other platelet inhibitors that act by a different mechanism. This is important not only for proper treatment of the patients, but also for cost savings. The other platelet inhibitors are much more expensive than aspirin, so it would be extremely expensive to indiscriminately prescribe them. (Other platelet inhibitors include ADP inhibitors such as ticlopidine, and monoclonal antibodies that block the GPI-IbIIIa receptor such as RHEOPRO.) Physicians are only likely to prescribe them when it can be shown that aspirin is not working.

Various techniques have been used to measure platelet function and aspirin resistance. Among these are platelet aggregation. In this technique, platelet-rich plasma was prepared from whole blood. ADP and arachidonic acid were added to activate the platelets. And aggregation of the platelets was measured by optical density changes. (Gum, P. A., et al., 2001, *Am. J Cardiology* 88: 230.) Another technique uses a device named the platelet function analyzer-100 (PFA-100). The PFA-100 uses a disposable cartridge with an aperture cut into a collagen-coated membrane infused with either ADP or epinephrine. Whole blood (approximately 1 ml) is pumped through the aperture at high shear rate. The blood comes into contact with the membrane where platelets adhere and aggregate. A platelet plug forms, occluding the aperture and stopping blood flow. The closure time is a measure of platelet function. (Gum, P. A., et al., 2001, *Am. J Cardiology* 88: 230.) Another device used to measure aspirin response is the Accumetrix VERIFYNOW Aspirin Assay (www.accumetrics.com/products/ultegra_asa.html). This product uses a turbidity-based optical detection system. The device contains fibrinogen-coated beads, and a platelet agonist. Blood is withdrawn, citrated, and then mixed with the coated beads and the agonist. Aggregation of the platelets to the beads is measured optically.

Prior tests for aspirin response have various drawbacks. Many use significant volumes of blood. Some require time-consuming and labor-consuming processing of the blood. And some measure adhesion and aggregation of the platelets, which are complex phenomena that are the end result of several interacting steps, rather than more directly measuring steps more directly related to aspirin's inhibition of cyclooxygenase.

A new method of monitoring aspirin response or response to other COX1 inhibitors is needed. Preferably, the method would use a small volume of blood (e.g., less than a drop), use unprocessed whole blood, be fast, and be relatively specific for the pathway inhibited by aspirin, the COX1 pathway.

SUMMARY

The invention involves a method to measure inhibition of platelet function by aspirin or another cyclooxygenase-1 inhibitor. Blood is withdrawn from a patient who has taken aspirin and mixed with a COX1-dependent platelet agonist, typically arachidonic acid, which is the substrate for the enzyme cyclooxygenase-1 in platelets. Arachidonic acid is converted in platelets by COX1 to $PGG_2$ and then to thromboxane $A_2$. Thromboxane $A_2$ is a potent activator of platelets and instigates the platelet release reaction, where the platelets secrete the contents of their dense bodies and alpha granules. One of the compounds secreted from the dense bodies is ATP. In the present method, the secreted extracellular ATP or other extracellular platelet-release-reaction product is detected, and its concentration is quantitatively or qualitatively determined. The result from the determination of the extracellular release-reaction product (e.g., ATP) concentration is compared with a standard, which can be the result from blood taken from the same patient before she or he took aspirin.

Aspirin acts by inactivating cyclooxygenase-1, the predominant cyclooxygenase in platelets. Thus, if aspirin has inactivated most or all cyclooxygenase-1, the amount of thromboxane $A_2$ produced will be decreased, the release reaction will be weaker, and less release reaction product (e.g., ATP) will be secreted, as compared to when the patient does not take aspirin.

The method can use less than a drop of blood. Whole blood can be used without any further processing. And results can be obtained at the patient's bedside in less than five minutes. In addition, since ATP release is strongly induced by thromboxane $A_2$, the assay has high specificity for the pathway inhibited by aspirin, the COX1 pathway: thromboxane $A_2$ synthesis from arachidonic acid.

In one embodiment, a finger prick is performed to draw a drop of blood from a patient who has not had aspirin or another COX1 inhibitor for at least several hours, preferably 8 days. (The lifetime of platelets is about 8 days. Aspirin covalently modifies the COX1 in platelets to inactivate it. So the effect of aspirin lingers until all the platelets inactivated by aspirin have been cleared. Other COX1 inhibitors may act by a noncovalent inhibition and have a shorter duration of action.) Approximately 2-10 µl of blood is taken and diluted 500:1 with buffer. The ATP-consuming and light-producing enzyme luciferase and its substrate luciferin are added, and a background reading of light emission is taken. Arachidonic acid is then added to the sample, and the increase in light emission is monitored. The patient then swallows aspirin, and the procedure is performed again, and the results compared. If the aspirin is working, there will be a large decrease in light emission in the blood sample drawn after the patient takes aspirin as compared to the sample drawn before the patient takes aspirin. If the patient is aspirin-resistant, the difference between the two results will be smaller.

Thus, one embodiment of the invention provides a method of monitoring COX1-inhibitor response involving: (a) collecting platelet-containing mammalian blood treated with a COX1 inhibitor; (b) mixing the blood with a COX1-dependent platelet agonist to generate agonist-activated blood; (c) monitoring an extracellular platelet-release-reaction product (e.g. ATP) in the agonist-activated blood to generate a measurement; and (d) comparing the measurement to a standard value.

Another embodiment of the invention provides a device for monitoring COX1-inhibitor response including: (a) a fluid-tight material forming an assay chamber; (b) a pump functionally linked to the assay chamber for pumping fluids into the assay chamber; (c) a light detector functionally linked to the assay chamber for detecting light emitted in the assay chamber; (d) a fluid-tight material forming a blood chamber for holding blood, the blood chamber functionally linked to the pump; (e) a fluid-tight material forming an enzyme chamber for holding a solution of a light-producing ATP-consuming enzyme, the enzyme chamber functionally linked to the pump; and (f) a fluid-tight material forming an agonist chamber for holding a solution of a COX1-dependent platelet agonist, the agonist chamber functionally linked to the pump.

Another embodiment of the invention provides a system for monitoring COX1-inhibitor response including: (a) a fluid-tight material forming an assay chamber; (b) a pump functionally linked to the assay chamber for pumping fluids into the assay chamber; (c) a light detector functionally linked to the assay chamber for detecting light emitted in the assay chamber; (d) a fluid-tight material forming a blood chamber for holding blood, the blood chamber functionally linked to the pump; (e) a fluid-tight material forming an enzyme chamber for holding a solution of a light-producing ATP-consuming enzyme, the enzyme chamber functionally linked to the pump; (f) a fluid-tight material forming an agonist chamber for holding a solution of a COX1-dependent platelet agonist, the agonist chamber functionally linked to the pump; (g) a controller coupled to the pump and programmed to deliver to the assay chamber a predetermined volume of the blood, a predetermined volume of the light-producing enzyme solution, and a predetermined volume of the agonist solution; and (h) a display operably coupled to the light detector for displaying results from the light detector.

In one embodiment of the invention, approximately 10 µl of whole blood is taken by a finger prick, and is mixed with arachidonic acid and placed in an assay chamber. The blood mixture in the assay chamber is physically agitated as light emission is monitored. The agitation activates the platelets, amplifying the activation by arachidonic acid. Arachidonic acid is relatively unstable on storage, and therefore assays of COX1 inhibitor response using arachidonic acid as agonist can be hampered by inconsistency in the activity of different batches of arachidonic acid. Physically agitating the sample makes the assay more tolerant of differences in the quality of the arachidonic acid added. Agitation also amplifies the effect of arachidonic acid, which speeds the release of ATP by the platelets (the ultimate amplitude of ATP release remains the same). This increases the signal, if the signal measured is the slope of the increase of light emission during the assay.

Thus, another embodiment of the invention provides a device for monitoring COX1 inhibitor response that includes: (a) a receptor adapted to hold an assay chamber; (b) a means for agitating fluid in the assay chamber, functionally linked to the assay chamber; and (c) a light detector functionally linked to the assay chamber for detecting light emitted in the assay chamber; wherein the device does not comprise a lamp for measuring platelet aggregation in the assay chamber.

Another embodiment of the invention provides a device for monitoring COX1 inhibitor response that includes: (a) a receptor adapted to hold an assay chamber; (b) an agitator functionally linked to the assay chamber to agitate fluid in the assay chamber; and (c) a light detector functionally linked to the assay chamber for detecting light emitted in the assay chamber; wherein the agitator is adapted to agitate fluid in the assay chamber by agitating the assay chamber or at least one wall of the assay chamber.

Another embodiment of the invention provides a disposable cuvette for use in a device to measure COX1 inhibitor response, the cuvette including: (a) a fluid-tight material forming an assay chamber for holding an assay mixture including blood, a light-producing ATP-consuming enzyme, and a COX1-dependent platelet agonist; and (b) a fluid-tight material forming a sealed but breakable reagent chamber that contains the light-producing ATP-consuming enzyme or the COX1-dependent platelet agonist, or both. The reagent chamber is designed on breakage to empty its contents into the assay chamber. The assay chamber includes a transparent window that allows light emission.

DETAILED DESCRIPTION

Definitions:

The term "COX1 inhibitor" refers to an agent that selectively inhibits COX1 more than it inhibits COX2 or inhibits COX1 at a lower concentration of agent than COX2. The inhibition can be due to covalent or noncovalent interactions. The inhibition can be inactivation, competitive, uncompetitive, or non-competitive inhibition. The most common COX1 inhibitor is aspirin. Another example of a COX1 inhibitor is SC-58560 (Bolla, M., et al., *Hypertension, Apr.* 19, 2004).

The term "platelet-containing blood" refers to whole blood or processed blood that contains platelets, e.g., platelet-rich plasma.

The terms "measurement" and "standard value" refer to quantitative or qualitative assessments that can be compared with each other.

The term "blood treated with a COX1 inhibitor" refers to blood contacted with a COX1 inhibitor either in vivo or ex situ. The blood can be contacted with the inhibitor (e.g., aspirin), e.g., by orally administering aspirin to a mammal, or by contacting blood with aspirin after withdrawing the blood from a mammal.

The term "dilution medium" refers to any suitable liquid for diluting blood. This typically is an aqueous solution that includes a pH buffer and solutes sufficient to maintain an appropriate osmoticum in the dilution buffer, such as phosphate buffered saline or HEPES/HANKS. Dilution medium, however, need not contain a pH buffer, and could be water or for instance, a salt or sucrose solution in water.

The term "ATP-consuming enzyme" refers to an enzyme that uses and consumes ATP as a substrate.

The term "chamber" refers to a vessel that contains fluids. The chamber can be substantially enclosed, or could be, for instance, a section of tubing in which liquid is held.

A "light detector" as used herein is any apparatus or component of an apparatus capable of qualitatively or, preferably, quantitatively determining the intensity of light or number of photons emitted in an assay chamber. An example of a light detector is a photon counter.

A "COX1-dependent platelet agonist" as used herein is an agonist whose activation of platelets is substantially inhibited by aspirin in aspirin-sensitive humans. Preferably, a COX1-dependent platelet agonist is an agonist that induces a maximal rate of extracellular ATP release in aspirin-sensitive humans in the assays described herein that is at least 5 times higher in non-aspirin-treated blood than in aspirin-treated blood. Conversely, a platelet agonist that is not COX1 dependent as used herein refers to an agonist whose activation of platelets is not substantially inhibited by aspirin in aspirin-sensitive humans. It induces a maximal rate of extracellular ATP release in aspirin-sensitive humans in the assays described herein that is less than 5 times higher, preferably less than 3 times higher, more preferably less than 2 times higher, most preferably approximately the same, in non-aspirin-treated blood than in aspirin-treated blood.

The most preferred COX1-dependent platelet agonist is arachidonic acid. The most preferred platelet agonist that is not COX1 dependent is thromboxane $A_2$. Other platelet agonists that are not COX1 dependent include collagen, thrombin, and ADP.

"An extracellular platelet-release-reaction product," as used herein, is a component secreted from platelets in response to arachidonic acid, whose maximal rate of secretion in aspirin-sensitive humans is at least 2 times faster before the person takes aspirin than the maximal rate of secretion after the person takes aspirin. Preferably, the platelet-release-reaction product is a product whose maximal rate of secretion is at least 3 times faster, more preferably at least 5 times faster, before the person takes aspirin than after the person takes aspirin. The extracellular platelet-release-reaction product may be soluble in the extracellular medium or may become exposed on the extracellular platelet membrane surface after the release reaction.

The preferred extracellular platelet-release-reaction product is ATP. Other examples of extracellular release reaction products include the dense body components GDP, GTP, ADP, serotonin, $Mg^{++}$, and $Ca^{++}$, as well as the alpha granule components fibrinogen, von Willebrand factor, fibronectin, thrombospondin, vitronectin, factor V, factor XI, protein S, platelet-derived growth factor, transforming growth factor β, epidermal growth factor, P-selectin, GMP 33, and osteonectin. (The Megakaryocyte-Platelet System, R. R. Rifkin, in *Clinical Hematology: Principles, Procedures, Correlations*, second edition, Stiene-Martin, E. A., et al., eds., Lippincott, N.Y., 1998.)

Figure 1:
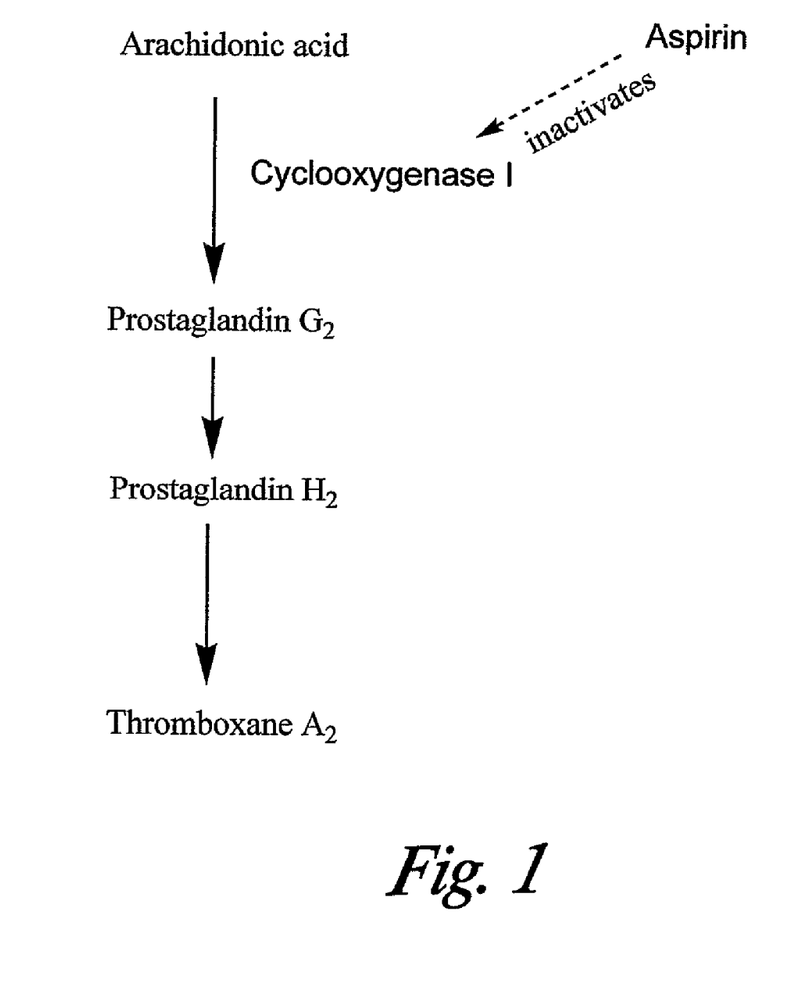
FIG. 1 shows the pathway of thromboxane $A_2$ synthesis from arachidonic acid.

Description:

The pathway of thromboxane $A_2$ synthesis from arachidonic acid in platelets is shown in FIG. 1. Aspirin inhibits this pathway by acetylating cyclooxygenase and inactivating the enzyme.

In one embodiment of the method of monitoring COX1-inhibitor response, the COX1 inhibitor is aspirin.

In one embodiment, the extracellular platelet-release-reaction product is ATP.

In one embodiment, the COX1-dependent platelet agonist is arachidonic acid.

Another example of a class of COX1-dependent platelet agonists is phospholipase $A_2$ activators. Compounds that activate phospholipase $A_2$ stimulate the release of arachidonic acid by the phospholipase $A_2$ in platelets.

Other specific examples of COX1-dependent platelet agonists include propyl gallate and U-46619 (Bolla, M. et al. *Hypertension*, Apr. 19, 2004.)

In one embodiment of the method of monitoring COX1-inhibitor response, the step of monitoring extracellular ATP involves adding to the blood an ATP-consuming enzyme that catalyzes a reaction, and monitoring the enzyme-catalyzed reaction.

In one embodiment, monitoring the enzyme-catalyzed reaction involves monitoring a product produced by the reaction. The product can be, for instance, light. In other embodiments, monitoring the reaction involves monitoring the disappearance of a reactant.

In one embodiment of the method using an enzyme, the enzyme is luciferase (e.g., firefly luciferase). In particular embodiments, the method further involves adding luciferin to the blood. In one embodiment, the luciferin is firefly luciferin.

The steps of the invention can be performed in any suitable order. For instance, in the embodiments that involve adding to the blood an ATP-consuming enzyme that catalyzes a reaction and monitoring the reaction, the enzyme can be added to the blood before, together with, or after the COX1-dependent agonist.

Likewise, where another enzyme substrate such as luciferin is added, the substrate can be added before, together with, or after both the enzyme and the agonist.

In one particular embodiment, luciferin and luciferase are added to the blood before the blood is mixed with the COX1-dependent platelet agonist. In another particular embodiment, luciferin and luciferase are added to the blood after the blood is mixed with the agonist.

Particular embodiments of the method of the invention further involve diluting the blood. The sensitivity of this method is such that whole blood can easily be diluted 1:1000 or more.

In a specific embodiment of the invention, the agonist-activated blood is diluted enough to prevent platelet aggregation. (The dilution of the blood preferably occurs before or while mixing the blood with the platelet agonist to generate agonist-activated blood.)

In specific embodiments, the agonist-activated blood is diluted at least 1/10, at least 1/20, or at least 1/100.

In a particular embodiment where the blood is diluted, the step of monitoring extracellular ATP involves adding luciferin and luciferase to the blood, and monitoring light produced by the luciferase.

One of the advantages of the method of the invention is that small volumes of blood can be used. Blood can be collected by a finger prick, and less than a drop can be used. In particular embodiments, less than 120, less than 100, less than 75, less than 40, less than 20, less than 12, or less than 10 microliters are collected from the mammal. In other particular embodiments, less than 120, less than 100, less than 75, less than 40, less than 20, less than 12, or less than 10 microliters of blood is mixed with the COX1-dependent platelet agonist.

In particular embodiments, the mammal is a human.

In particular embodiments of the invention, the platelet-containing blood is whole blood.

A particular embodiment of the invention provides a method of monitoring COX1 inhibitor response involving collecting less than 100 μl whole blood from a mammal, wherein the blood is treated in vivo or ex situ with a COX1 inhibitor; mixing the blood treated with a COX1 inhibitor with a COX1-dependent platelet agonist to generate agonist-activated blood; monitoring an extracellular platelet-release-reaction product in the agonist-activated blood to generate a measurement; and comparing the measurement to a standard value.

One method of determining the standard value for comparison in the assay is to collect non-aspirin-treated blood (or blood not treated with a COX1 inhibitor) from the same mammalian subject, and perform the same assay on the non-aspirin-treated blood to generate a measurement to be used as the standard value. In these embodiments, the standard value is determined by a method involving collecting platelet-containing standard blood from the mammal; mixing the standard blood with the COX1-dependent platelet agonist to generate agonist-activated standard blood; and monitoring the extracellular platelet-release-reaction product (e.g., ATP) in the agonist-activated standard blood to generate the standard value; wherein the standard blood is not treated with the COX1 inhibitor. Preferably, the mammalian subject has not been treated with the COX1 inhibitor for at least 3 hours, more preferably at least 6 hours, more preferably at least 12 hours, and more preferably still at least 24 hours, and most preferably at least 8 days before the blood is collected. If the COX1 inhibitor is aspirin, preferably the subject has not been treated with aspirin for at least 24 hours, more preferably for at least 3 days, and more preferably still for at least 8 days before the blood is collected.

The standard value can be obtained also by assaying blood of subjects different from the subject whose COX1-inhibitor-treated blood is assayed, and establishing a typical measured value reflecting the extracellular platelet-release-reaction product in agonist-activated blood where the blood is not COX1-inhibitor treated or where the blood is COX1-inhibitor-treated from subjects either resistant or sensitive to the COX1 inhibitor.

The measurement and standard value can be quantitative or qualitative, and can be time courses or individual time points. For instance, the measurement and standard value can be direct measurements of extracellular ATP concentration at a certain time point after mixing the blood with the agonist. They can also be time courses of light emission using luciferin or luciferase or individual time points of quantity of light emitted at a specific time after agonist mixing using luciferin and luciferase.

Another potential measurement is to determine the amount of extracellular platelet-release-reaction product (e.g., ATP) secreted due to the agonist, then lyse the platelets with detergent such as TRITON X-100 or SDS, and determine the extracellular platelet-release-reaction product after platelet lysis, which represents the total cellular product. The measurement and standard value can be the difference in product (e.g., ATP) concentration before and after detergent lysis, or the ratio of product concentration before cell lysis to product concentration after cell lysis. That difference or ratio measurement can be compared between blood treated with the COX1 inhibitor (the measurement) and blood not treated with the COX1 inhibitor (the standard).

In a particular embodiment, the standard value is determined by a method involving: (a) collecting platelet-containing standard blood from the mammal; (b) diluting the standard blood; (c) mixing the standard blood with the COX1-dependent platelet agonist to generate agonist-activated standard blood; and (d) monitoring extracellular ATP in the agonist-activated standard blood to generate the standard value, wherein the step of monitoring extracellular ATP involves (i) adding luciferin and luciferase to the standard blood, and (ii) monitoring light produced by the luciferase; wherein the standard blood is not treated with the COX1 inhibitor.

In a particular embodiment of that method, luciferin and luciferase are added to the standard blood before mixing the standard blood with the agonist (e.g., arachidonic acid). In another, less preferred, embodiment, they are added after mixing the standard blood with agonist.

Thus, in one embodiment, a result of assaying for the extracellular platelet-release-reaction product (e.g., ATP) in agonist-activated COX1-inhibitor-treated blood is compared with a result obtained using blood not treated with the COX1 inhibitor, preferably from the same individual.

In one embodiment, a result of assaying for the extracellular platelet-release-reaction product in arachidonic-acid-activated aspirin-treated blood is compared with a result obtained using non-aspirin-treated blood, preferably from the same individual.

The results from COX1-dependent agonist treatment can also be compared to results obtained using an agonist that is not COX1 dependent. For instance, the amount of extracellular platelet-release-reaction product in arachidonic-acid-activated COX1-inhibitor-treated blood can be compared with the amount of extracellular platelet-release-reaction product in thromboxane-$A_2$-activated COX1-inhibitor-treated blood. Thromboxane $A_2$ is the end product of the cyclooxygenase-1 pathway, the target of aspirin. So thromboxane $A_2$ will activate platelets to the same extent whether or not they are treated with a COX1 inhibitor such as aspirin and whether or not the platelets are sensitive to the COX1 inhibitor. In contrast, arachidonic acid will activate platelets to a much greater extent if the platelets are not treated with the COX1 inhibitor or are insensitive to the COX1 inhibitor.

Likewise, aspirin is also not expected to have as large an effect on the extent of platelet activation by certain other activators, including thrombin, collagen, and ADP, as it does on the extent of platelet activation by arachidonic acid. Thus, the amount of extracellular ATP induced by arachidonic acid activation can be compared to the amount of extracellular ATP induced by activation with thrombin, collagen, or ADP.

Accordingly, in certain embodiments of the invention, the standard value is determined by a method involving: collecting platelet-containing COX1-inhibitor-treated standard blood from the mammal; mixing the standard blood with a non-COX1-dependent platelet agonist to generate activated standard blood; and monitoring the extracellular platelet-release-reaction product (e.g., ATP) in the activated standard blood to generate the standard value. The non-COX1-dependent platelet agonist can be, for instance, thromboxane $A_2$, thrombin, collagen, or ADP.

Where the extracellular platelet-release-reaction product is ATP, a preferred method of detecting the ATP is by enzymatic methods, as described herein, in particular by the use of luciferin. ATP can also be detected, for example, by HPLC or gas chromatography, with or without mass spectrometry. Other extracellular platelet-release-reaction products can also be detected by HPLC, gas chromatography, and/or mass spectrometry. Some platelet-release-reaction products can be detected by enzymatic means, where for instance the release reaction product is a substrate for an enzymatic reaction, and the course of the enzymatic reaction is monitored by monitoring a product of the enzymatic reaction. Some extracellular platelet-release-reaction products, particularly proteins, are amenable to detection by immunologic means, such as ELISA.

In one embodiment of the methods of the invention, the method further includes before or during the monitoring step, agitating the blood in such a manner as to enhance platelet activation by the agonist. Preferably in this embodiment, the blood is agitated as it is mixed with the agonist. As discussed in the summary section, arachidonic acid is fairly unstable on storage, and so different batches of arachidonic acid can have different activity levels. Physically mixing or agitating platelets activates them, and so amplifies the activation by arachidonic acid. The agitation thus makes the assay less sensitive to variations in the quality of arachidonic acid (or other agonist) used. The agitation also accelerates the rate of ATP release with arachidonic acid and other agonists. Thus, if rate of ATP release is measured, the signal is larger when agitation is combined with adding a platelet agonist.

In particular embodiments of the invention, the blood is not agitated in such a manner as to enhance platelet activation by the platelet agonist.

Figure 3:
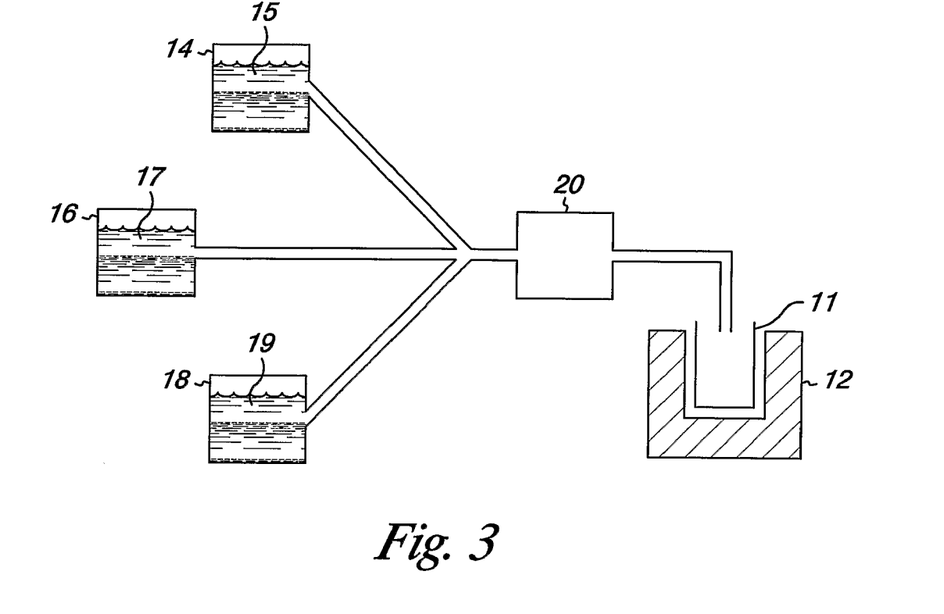
FIG. 3 is a schematic diagram of a device for monitoring COX1 inhibitor response.

The invention also provides a device, schematically shown in FIG. 3, having a fluid-tight material forming an assay chamber 11, a pump 20 for pumping fluids into the assay chamber, and a light detector 12 for detecting light emitted in the assay chamber. The device also includes a fluid-tight material forming a blood chamber 14 for holding blood 15, the blood chamber functionally linked to the pump 20. The device also includes a fluid-tight material forming an enzyme chamber 16 for holding a solution of a light-producing enzyme 17, the enzyme chamber functionally linked to the pump 20. The device also includes a fluid-tight material forming an agonist chamber 18 for holding a solution of a COX1-dependent platelet agonist 19, the agonist chamber functionally linked to the pump 20. The "solution" of a COX1-dependent platelet agonist can be pure agonist or undissolved agonist in suspension, but preferably is a true solution of the agonist (e.g., arachidonic acid) dissolved in water, ethanol, or another solvent.

Figure 4:
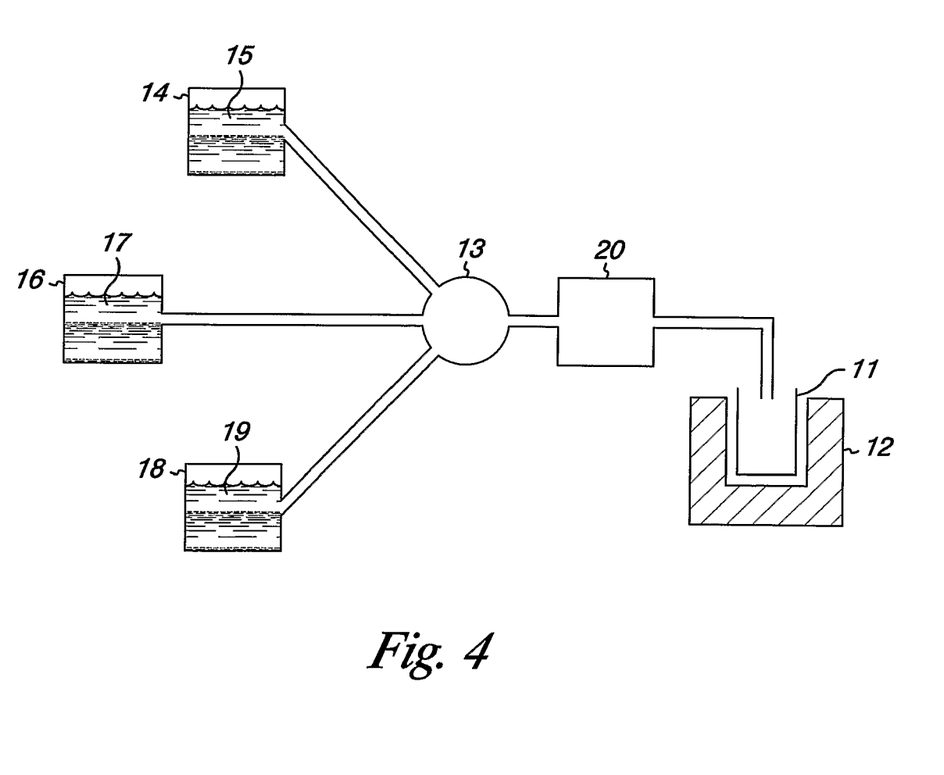
FIG. 4 is a schematic diagram of a device for monitoring COX1 inhibitor response, where the device includes a valve.

In one embodiment, the device further includes a valve 13 functionally linked to the pump, the assay chamber, the blood chamber, the enzyme chamber, and the agonist chamber (FIG. 4). The valve can be, for instance, a multi-position valve.

In one embodiment, the device further includes a fluid-tight material forming a dilution medium chamber for holding dilution medium, the dilution medium chamber functionally linked to the pump.

Two or three of the assay chamber, the blood chamber, the enzyme chamber, and the agonist chamber can be the same chamber.

In one embodiment, all of the four chambers—the assay chamber, the blood chamber, the enzyme chamber, and the agonist chamber—are separate chambers.

Figure 5:
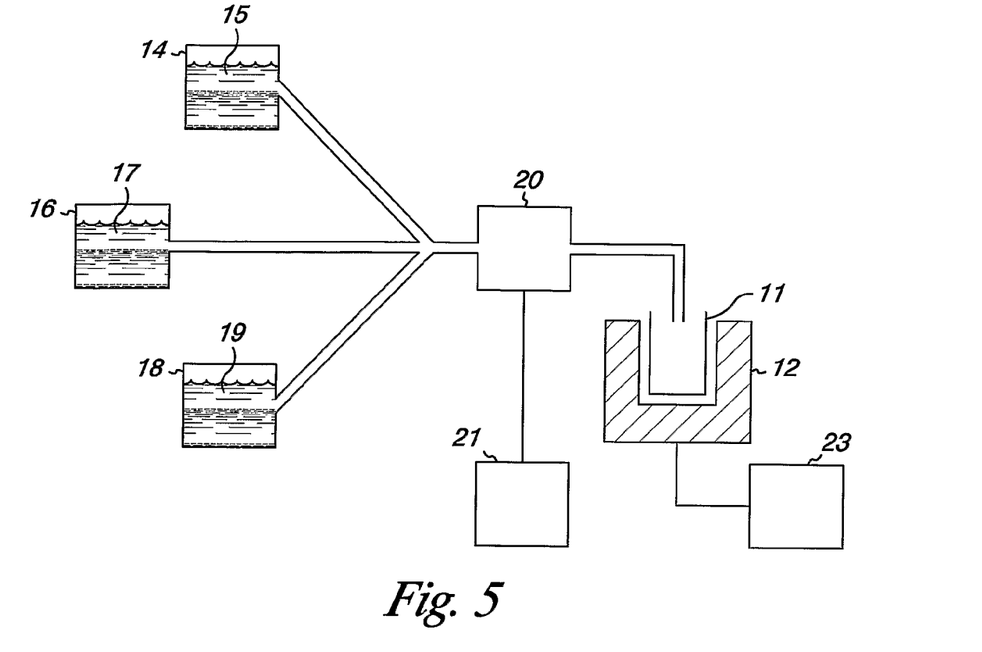
FIG. 5 is a schematic diagram of a system for monitoring COX1 inhibitor response.

The invention also provides a system for monitoring aspirin response involving all the elements of the device, along with a controller 21 for delivering to the assay chamber a predetermined volume of the blood, a predetermined volume of the light-producing enzyme solution, and a predetermined volume of the agonist solution; and a display 23 linked to the light detector for displaying light detector results (FIG. 5).

In particular embodiments, the predetermined volume of blood is less than 120, less than 100, less than 75, less than 40, less than 20, less than 12, or less than 10 microliters.

One embodiment of the invention provides a kit for determining response to a COX1 inhibitor (e.g., aspirin) involving a COX1-dependent platelet agonist (e.g., arachidonic acid), an ATP-consuming enzyme, and instruction means.

In one embodiment of the kit, the enzyme is a light-producing ATP-consuming enzyme.

Figure 7:
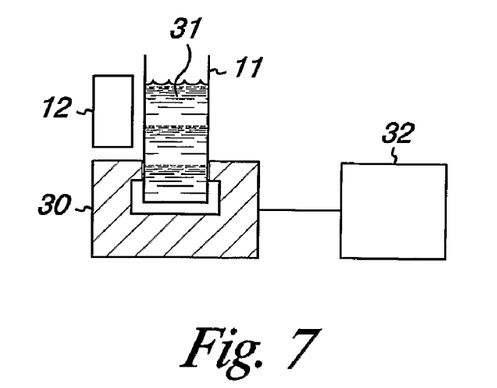
FIG. 7 is a diagram of a device for monitoring COX1 inhibitor response that pumps fluids into a cuvette.

One embodiment of the invention, shown in FIG. 7, provides a device for monitoring COX1 inhibitor response that includes: (a) a receptor 30 adapted to hold an assay chamber; (b) a means 32 for agitating fluid in the assay chamber, functionally linked to the assay chamber; and (c) a light detector 12 functionally linked to the assay chamber for detecting light emitted in the assay chamber; wherein the device does not comprise a lamp for measuring platelet aggregation in the assay chamber.

The means 32 for agitating fluid 31 in the assay chamber can be any suitable means that produces enough physical mixing to activate the platelet release reaction, at least with the assistance of a platelet agonist. This can be a stir bar in the assay chamber linked to a motor to rotate the stir bar. The means for agitating fluid in the assay chamber can also be a pump to pump fluid through a passageway, where the assay chamber is a section of the passageway or the whole passageway. It is preferred in this embodiment that there be an obstruction in the passageway, such as an abrupt narrowing of the passageway. Platelets are activated by the change in shear as they pass the obstruction. Another embodiment of the means for agitating fluid in the assay chamber is an agitator adapted to agitate fluid in the assay chamber by agitating the assay chamber or at least one wall of the assay chamber. A cellular phone vibrator, for instance, can be used to vibrate or agitate the assay chamber. The agitator may be directly linked to assay chamber or may be linked to agitate the receptor adapted to hold the assay chamber.

In a particular embodiment, the device further comprises the assay chamber 11, held in the receptor.

In a particular embodiment, the assay chamber further comprises 1-99 µl of whole blood, as well as a COX1-dependent platelet agonist, and an ATP-consuming light-producing enzyme.

In a particular embodiment, the assay chamber has a capacity for less than 300 µl of fluid.

In a particular embodiment, the means for agitating fluid is an agitator adapted to agitate fluid in the assay chamber by agitating the assay chamber or at least one wall of the assay chamber.

In particular embodiments of the devices of the invention, the device is adapted to be hand held. For instance, in one embodiment, the device or at least one section of the device is less than about 5 cm thick and less than about 10 cm wide.

Figure 8:
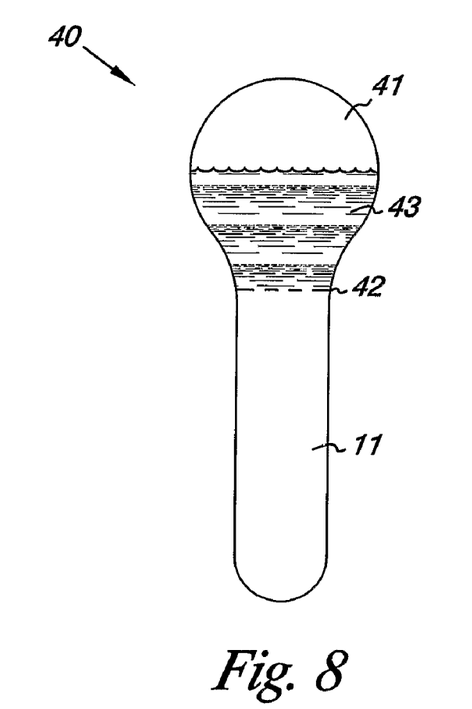
FIG. 8 is a diagram of a disposable cuvette of the invention for use in a device for monitoring COX1 inhibitor response.

Another embodiment of the invention, shown in FIG. 8, provides a disposable cuvette 40 for use in a device to measure COX1 inhibitor response. The cuvette 40 includes: (a) a fluid-tight material forming an assay chamber 11 for holding an assay mixture including blood, a light-producing ATP-consuming enzyme, and a COX1-dependent platelet agonist; and (b) a fluid-tight material forming a sealed but breakable reagent chamber 41 that contains the light-producing ATP-consuming enzyme or the COX1-dependent platelet agonist, or both. The reagent chamber 41 is designed on breakage to empty its contents 43 into the assay chamber 11. The assay chamber 11 includes a transparent window that allows light emission. The window can be just a part of a wall of the assay chamber or can be the entire wall of the assay chamber.

FIG. 8 shows a particular embodiment of the disposable cuvette 40 where the reagent chamber 41 is separated from the assay chamber 11 by a breakable barrier. In FIG. 8 the reagent chamber is shown as squeezable bulb with flexible walls. Squeezing the walls of reagent chamber 41 increases the pressure in the reagent chamber causing barrier 42 to break, allowing the contents 43 of the reagent chamber to flow into assay chamber 11.

In a particular embodiment of the disposable cuvette, the reagent chamber contains the COX1-dependent platelet agonist, where the agonist is arachidonic acid, and the reagent chamber is gas tight and contains no $O_2$. Molecular oxygen can oxidize arachidonic acid. Thus, the arachidonic acid is more stable if it is stored in a gas-tight chamber free of oxygen.

The invention will now be illustrated by the following non-limiting examples.

EXAMPLES

Example 1

Assaying platelet aspirin response.

Methods:

Volunteers who had not taken aspirin in the previous 24 hours underwent a finger prick to draw blood. Blood (2 µl) was diluted into 1 ml of buffer (PBS, 0.9% NaCl, 10 mM sodium phosphate, pH 7.0) in a clear test tube. An aliquot (15 µl) of luciferin/luciferase solution (containing 10 mg/ml luciferin and 10 µg/ml luciferase) was added to the diluted blood. The solution was mixed and placed in a Zylux FEMP-TOMASTER FB12 photon counter. A baseline reading of the light emission was taken. The test tube was then withdrawn, and 5 µl of 15 mM arachidonic acid was added to the solution and the solution was mixed. The test tube was then reinserted in the photon counter and light emission readings were taken for approximately 2 to 4 minutes.

The volunteer then swallowed or chewed an aspirin (325 mg). A blood sample was taken, and the process was repeated. The results from blood drawn from an individual before and after taking aspirin were compared.

Figure 2A:
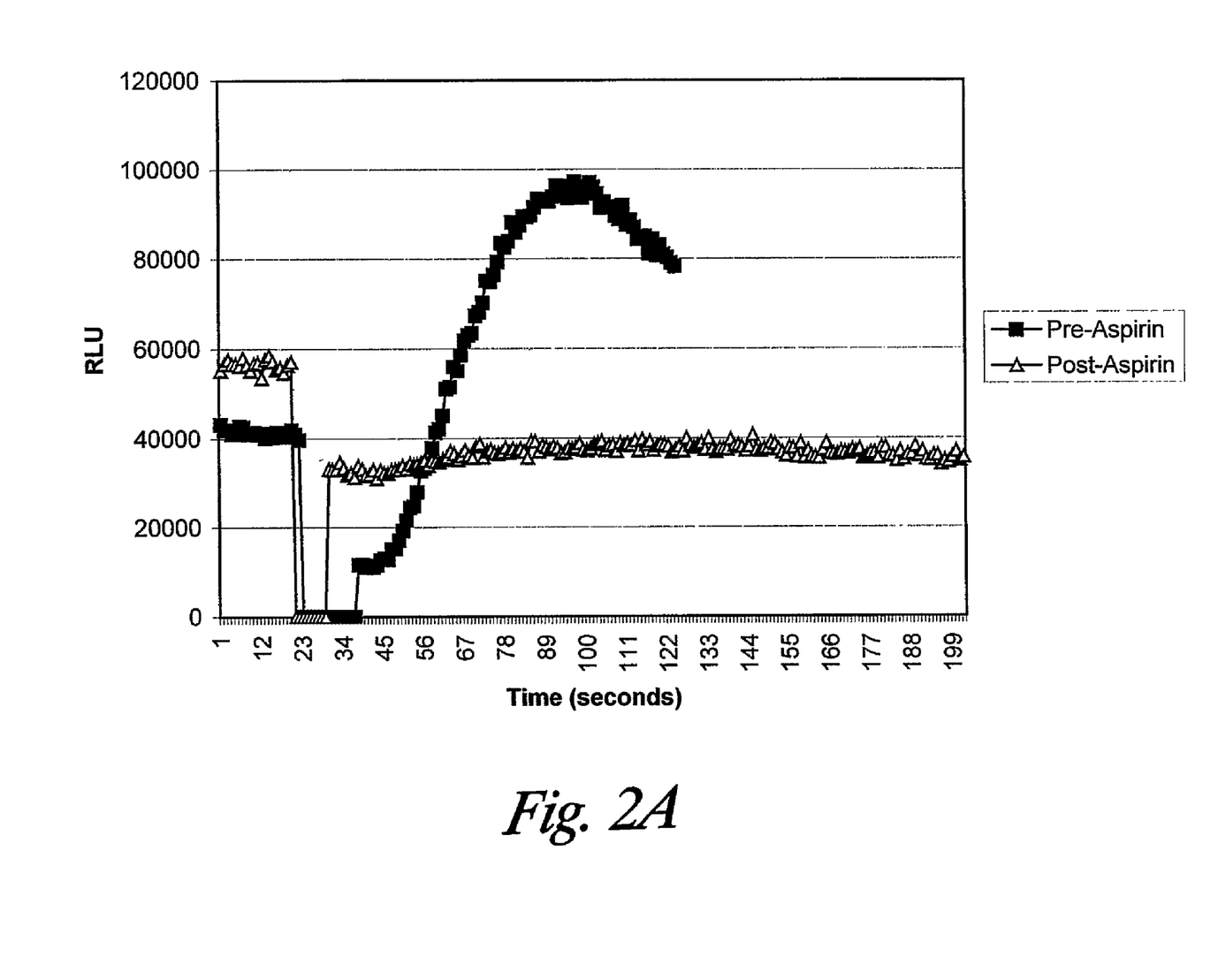
FIGS. 2A-C show luciferase assay results with arachidonic-acid-treated diluted blood drawn from three individuals before and after taking aspirin. The light emission reflects extracellular ATP.
Figure 2B:
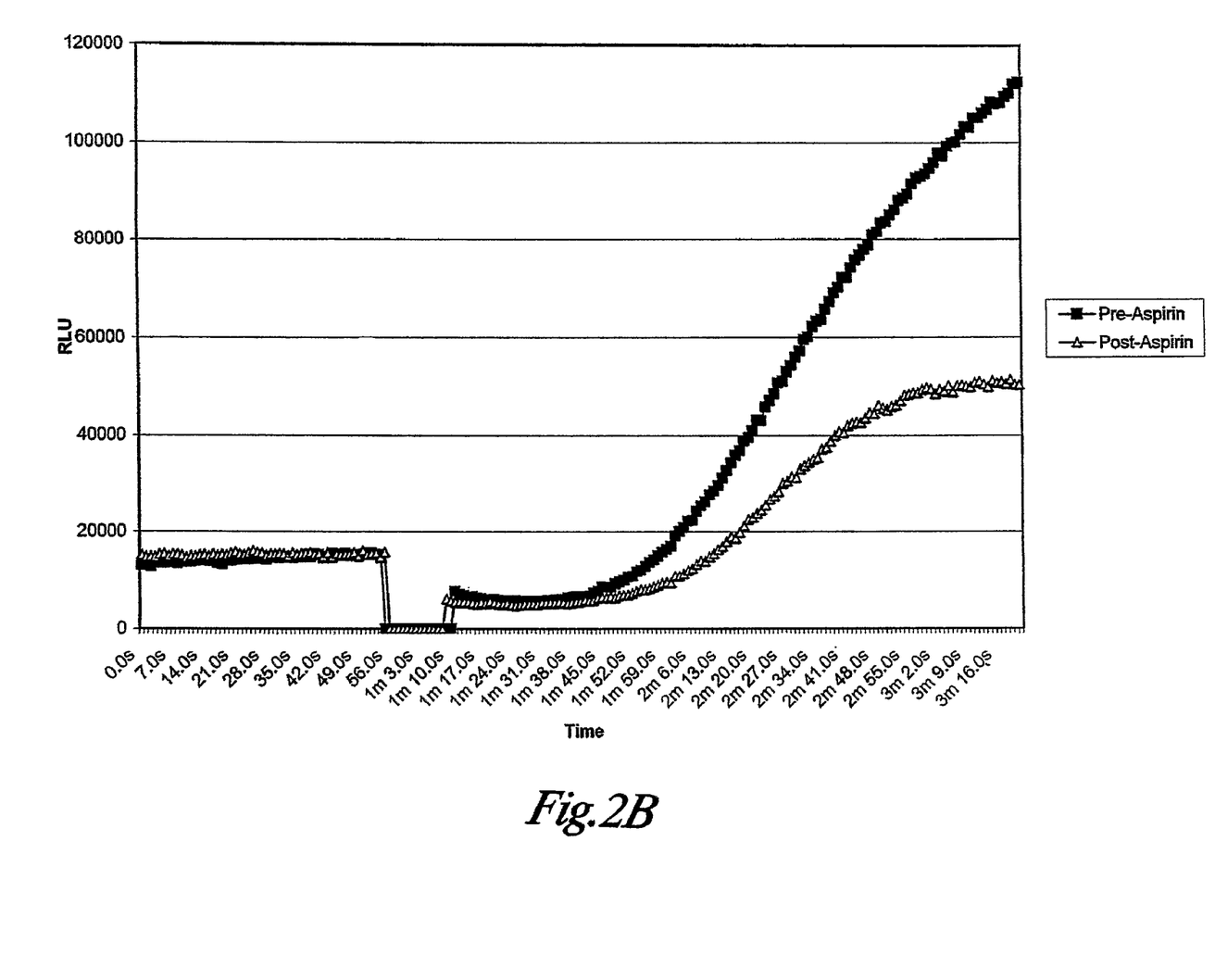
Figure 2C:
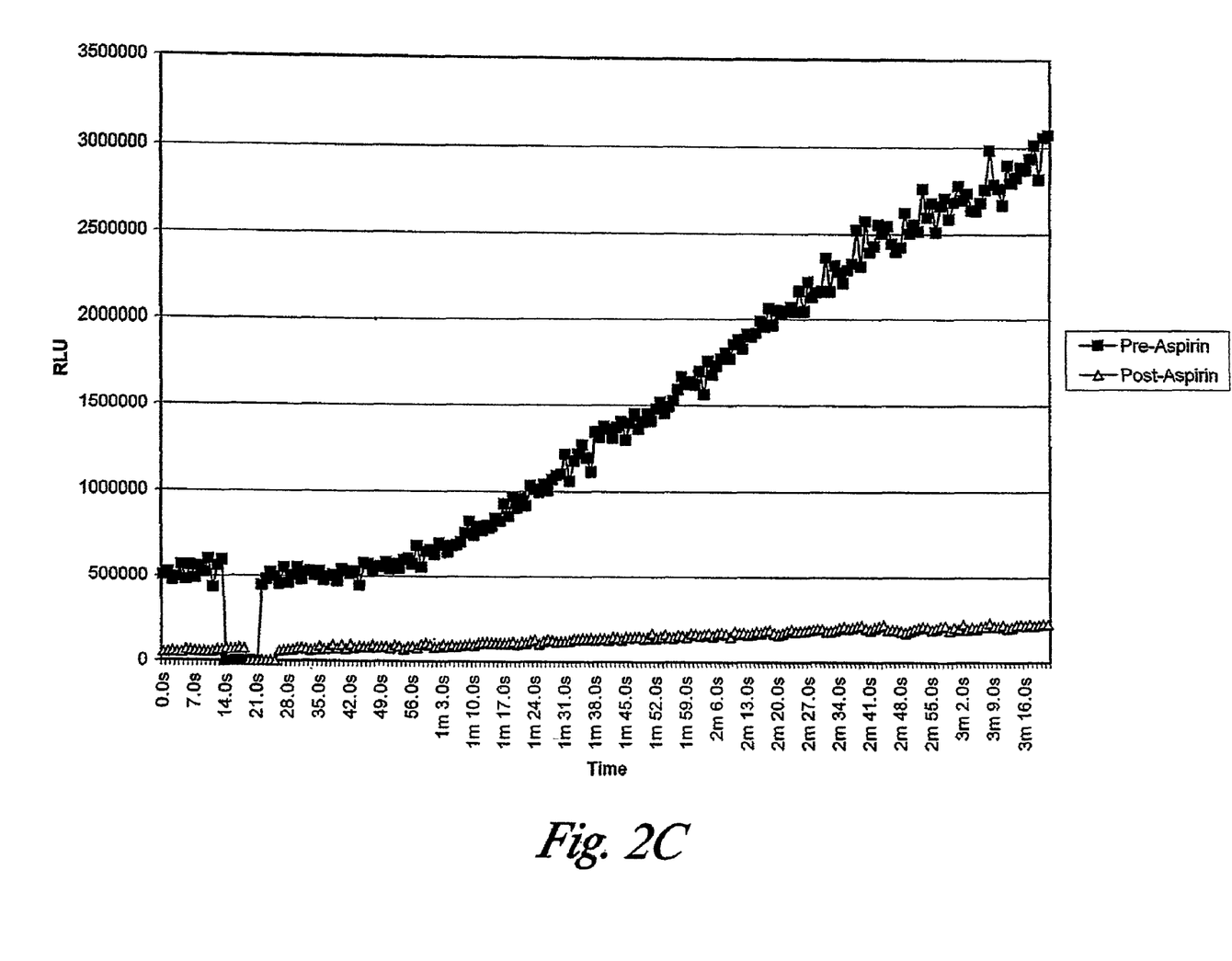

Results: p Time courses of light emission in the assays for three individuals before and after taking aspirin are shown in FIGS. 2A-C. In FIGS. 2A and 2C the slope of light emission vs. time after arachidonic acid is added to the sample is very steep for the no-aspirin sample but almost flat for the aspirin sample. The ratio of the no-aspirin maximal slope to the aspirin maximal slope is greater than 10:1. In contrast, results for the individual of FIG. 2B show a ratio of maximal slopes of the no-aspirin to the aspirin sample of slightly less than 2:1. Thus, the individual of FIG. 2B is less responsive to aspirin than the individuals of FIGS. 2A and 2C.

Discussion:

A very small amount of blood was used in this assay—2 µl—easily less than a drop of blood. Even less could be used. The limiting factor for using smaller volumes would probably be inaccuracy of measuring the volumes, which would cause imprecision in the assay results.

Lesser amounts of luciferin, luciferase, and arachidonic acid could be used than were used in this example. With lower amounts of luciferin or luciferase, the light emission would plateau sooner and at lower levels. The inventor believes that instead of the 15 mM arachidonic acid solution used in this example, 10 µM or less and possibly 1 µM or less arachidonic acid could be used without affecting the results.

To determine aspirin response, the data can be analyzed in several ways. The maximal slopes of the no-aspirin and aspirin samples can be compared. The peak light emission levels can be compared. The light emission at a certain time after adding arachidonic acid to the blood, e.g., 2 minutes, can be compared. Or a difference in light emission levels can be calculated for each sample and then compared, e.g., light emission at 2 minutes after adding arachidonic acid minus emission at 10 seconds after adding arachidonic acid or minus emission before adding arachidonic acid.

Example 2

An apparatus for monitoring aspirin response that pumps fluids into a cuvette.

Figure 6:
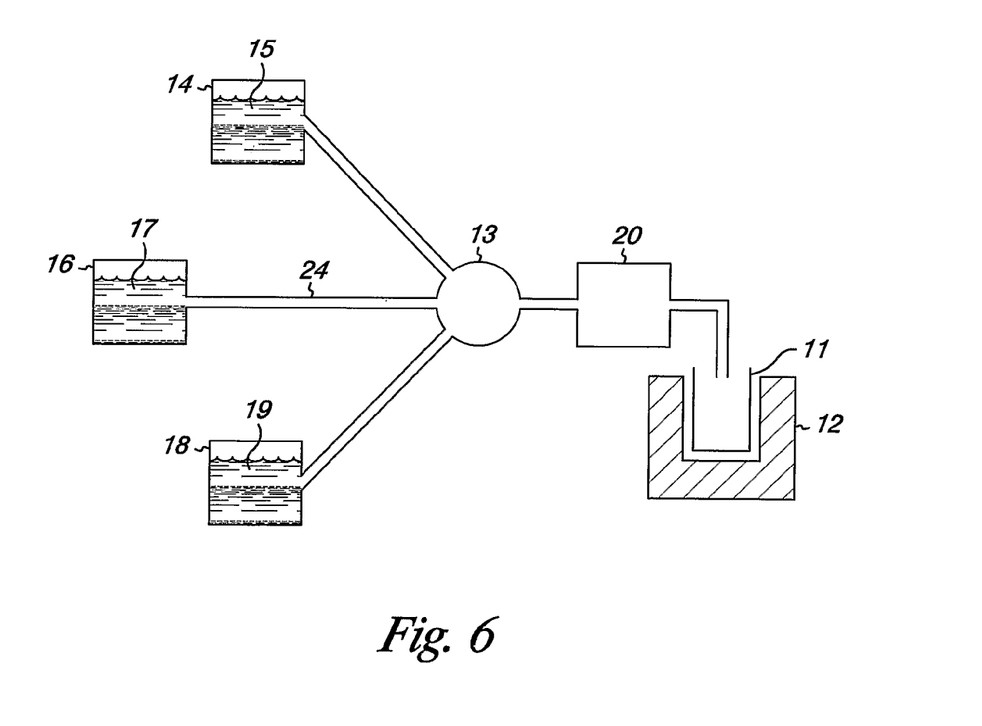
FIG. 6 is a diagram of a particular apparatus for monitoring aspirin response that pumps fluids into an assay chamber.

The apparatus is shown in FIG. 6. Blood is diluted and stored in a diluted blood chamber or container 14. Firefly luciferin and luciferase are stored in a firefly extract container 16. Arachidonic acid is stored in a third container, an arachidonic acid container 18. Tubing 24 connects the solutions in each container to a bi-directional pump 20. The tubing to the three containers merges together before the pump, so that fluid is pumped by the pump simultaneously from all three containers and mixed together. If the tubing to each container is the same diameter, equal volumes are pumped from each container. By using tubing of unequal diameters to each container, the volume drawn from each container relative to the others can be controlled. The drawn fluids come together in the merged section of the tubing and are pulled by the pump 20 past a check valve 13. After the check valve the fluids are pumped by the bi-directional pump to an assay chamber 11 positioned within a photon counter 12 such as a photomultiplier tube. In the assay chamber 11, the fluids are further mixed, either by brownian motion or by a mechanical mixer, and the photons emitted are counted by the photon counter.

The pump and photon counter are preferably microprocessor controlled.

Example 3

Fluid Injection Analysis and Sequential Injection Analysis

A typical fluid injection analysis (FIA) manifold includes a pump, injection valve, photon counter, and tubing. The pump is used to propel one or more streams through the photon counter via a narrow-bore (0.5-0.8 mm ID) tubing. These streams may be reagents or buffer. The injection valve is used to periodically introduce a small volume (generally less than 100 µl) sample of one reagent into the carrier stream. As the sample is carried to the detector, the fluid dynamics of flow through a narrow-bore tubing mixes sample and carrier, leading to the reaction to form a detectable species (in this case light emission). This species is sensed by the detector as a transient peak. The height and area of the peak are proportional to concentration and are used to quantify the concentration of the species being determined by comparison to samples of known concentration (a calibration curve). Thus, for instance, blood, dilution buffer, and luciferin/luciferase can be premixed in the carrier stream, and arachidonic acid can be the injectable reagent added last to start the reaction.

In sequential injection analysis, a selection valve and a bi-directional pump are used to draw up small volumes of sample and reagents, and then propel them through a coil to a detector. Again the process causes mixing of the sample and reagent segments leading to chemistry that forms a detectable species before reaching the detector.

A type of sequential injection analysis device that could be adapted for use in the invention is described in U.S. Pat. No. 6,716,391.

Information and supplies for fluid injection analysis and sequential injection analysis are available at www.globalfia.com, Global FIA, Inc., Fox Island, Wash.

All cited patents, patent-related documents, and other references are incorporated by reference.

What is claimed is:

1. A device for monitoring cyclooxygenase-1 (COX1) -inhibitor response comprising:
    a predetermined volume of a solution of light-producing ATP-consuming enzyme;
    a predetermined volume of a solution of COX1-dependent platelet agonist;
    a fluid-tight material forming an assay chamber;
    a pump functionally linked to the assay chamber for pumping fluids into the assay chamber;
    a light detector functionally linked to the assay chamber for detecting light emitted in the assay chamber;
    a fluid-tight material forming a blood chamber for holding blood, the blood chamber functionally linked to the pump;
    a fluid-tight material forming an enzyme chamber for holding the predetermined volume of the solution of the light-producing ATP-consuming enzyme, the enzyme chamber functionally linked to the pump; and
    a fluid-tight material forming an agonist chamber for holding the predetermined volume of the solution of the COX1-dependent platelet agonist, the agonist chamber functionally linked to the pump.

2. The device of claim 1 further comprising a valve functionally linked to the pump, the assay chamber, the blood chamber, the enzyme chamber, and the agonist chamber.

3. The device of claim 1 further comprising a fluid-tight material forming a dilution medium chamber for holding a solution of a dilution medium, the dilution medium chamber functionally linked to the pump.

4. The device of claim 1 wherein two of the assay chamber, the enzyme chamber, the blood chamber, and the agonist chamber are the same chamber.

5. The device of claim 1 wherein three of the assay chamber, the enzyme chamber, the blood chamber, and the agonist chamber are the same chamber.

6. The device of claim 1 wherein the assay chamber, the enzyme chamber, the blood chamber, and the agonist chamber are separate chambers.

7. A system for monitoring cyclooxygenase-1 (COX1)-inhibitor response comprising:
   a predetermined volume of a solution of light-producing ATP-consuming enzyme;
   a predetermined volume of a solution of COX1-dependent platelet agonist;
   a fluid-tight material forming an assay chamber;
   a pump functionally linked to the assay chamber for pumping fluids into the assay chamber;
   a light detector functionally linked to the assay chamber for detecting light emitted in the assay chamber;
   a fluid-tight material forming a blood chamber for holding blood, the blood chamber functionally linked to the pump;
   a fluid-tight material forming an enzyme chamber for holding a solution of a light-producing ATP-consuming enzyme, the enzyme chamber functionally linked to the pump;
   a fluid-tight material forming an agonist chamber for holding a solution of a COX1-dependent platelet agonist, the agonist chamber functionally linked to the pump;
   a controller coupled to the pump and programmed to deliver to the assay chamber a predetermined volume of the blood, the predetermined volume of the light-producing enzyme solution, and the predetermined volume of the agonist solution; and
   a display operably coupled to the light detector for displaying results from the light detector.

8. The system of claim 7 further comprising a valve functionally linked to the pump, the assay chamber, the blood chamber, the enzyme chamber, and the agonist chamber.

9. The system of claim 7 wherein the predetermined volume of blood is less than 40 µl.

10. A device for monitoring cyclooxygenase-1 (COX1)-inhibitor response comprising:
    a predetermined volume of a solution of light-producing ATP-consuming enzyme;
    a predetermined volume of a solution of COX1-dependent platelet agonist;
    a fluid-tight material forming an assay chamber;
    a receptor adapted to hold the assay chamber;
    a means for delivering the predetermined volume of the solution of light-producing ATP-consuming enzyme, the predetermined volume of the solution of COX1-dependent platelet agonist, and a volume of blood into the assay chamber, wherein the means comprises a pump;
    a means for agitating fluid in the assay chamber, functionally linked to the assay chamber; and
    a light detector functionally linked to the assay chamber for detecting light emitted in the assay chamber;
    wherein the device does not comprise a lamp for measuring platelet aggregation in the assay chamber.

11. The device of claim 10 wherein the volume of blood is in a range of 1-99 µl whole blood.

12. The device of claim 10 wherein the assay chamber has a capacity for less than 300 µl of fluid.

13. The device of claim 10 wherein the means for agitating fluid includes an agitator adapted to agitate fluid in the assay chamber by agitating the assay chamber.

14. The device of claim 10 wherein the device is adapted to be hand held.

15. The device of claim 10 wherein the means for agitating fluid includes means for agitating at least one wall of the assay chamber.

16. A device for monitoring cyclooxygenase-1 (COX1)-inhibitor response comprising:
    a predetermined volume of a solution of light-producing ATP-consuming enzyme;
    a predetermined volume of a solution of COX1-dependent platelet agonist;
    a fluid-tight material forming an assay chamber;
    a receptor adapted to hold the assay chamber;
    a fluid-delivery system functionally linked to the assay chamber and configured to deliver the predetermined volume of the solution of light-producing ATP-consuming enzyme, the predetermined volume of the solution of COX1-dependent platelet agonist, and a volume of blood into the assay chamber, wherein the fluid-delivery system comprises a pump;
    an agitator functionally linked to the assay chamber to agitate fluid in the assay chamber; and
    a light detector functionally linked to the assay chamber for detecting light emitted in the assay chamber.

17. A device for monitoring cyclooxygenase-1(COX 1)-inhibitor response comprising:
    a predetermined volume of a solution of light-producing ATP-consuming enzyme;
    a predetermined volume of a solution of COX1-dependent platelet agonist;
    a fluid-tight material forming an assay chamber;
    a fluid-moving structure functionally linked to the assay chamber for moving fluids into the assay chamber, wherein the fluid-moving structure commprises a pump;
    a light detector functionally linked to the assay chamber for detecting light emitted in the assay chamber;
    a fluid-tight material forming a blood chamber for holding blood, the blood chamber functionally linked to the fluid-moving structure;
    a fluid-tight material forming an enzyme chamber for holding the predetermined volume of the solution of the light-producing ATP-consuming enzyme, the enzyme chamber functionally linked to the fluid-moving structure; and
    a fluid-tight material forming a reagent chamber for holding the predetermined volume of the solution of the COX1-dependent platelet agonist, the agonist chamber functionally linked to the fluid-moving structure.

18. The device for monitoring COX1 inhibitor response of claim 17, wherein:
    at least the reagent chamber and the assay chamber are formed in a disposable structure.

19. The device for monitoring COX1 inhibitor response of claim 18, wherein:
    the disposable structure is a disposable cuvette.

20. The device of claim 19, wherein the reagent chamber of the disposable cuvette contains COX1-dependent platelet agonist, the agonist is arachidonic acid, and the reagent chamber is gas tight and contains no $O_2$.

21. A device for monitoring inhibition of platelet function response comprising:

a predetermined volume of a solution of light-producing ATP-consuming enzyme;

a predetermined volume of a solution of platelet agonist;

a fluid-tight material forming an assay chamber;

a pump functionally linked to the assay chamber for pumping fluids into the assay chamber;

a light detector functionally linked to the assay chamber for detecting light emitted in the assay chamber;

a fluid-tight material forming a blood chamber for holding blood, the blood chamber functionally linked to the pump;

a fluid-tight material forming an enzyme chamber for holding the predetermined volume of the solution of the light-producing ATP-consuming enzyme, the enzyme chamber functionally linked to the pump; and a fluid-tight material forming an agonist chamber for holding the predetermined volume of the solution of the platelet agonist, the agonist chamber functionally linked to the pump.

22. The device of claim 21, further comprising a valve functionally linked to the pump, the assay chamber, the blood chamber, the enzyme chamber, and the agonist chamber.

23. The device of claim 21, further comprising a fluid-tight material forming a dilution medium chamber for holding a solution of a dilution medium, the dilution medium chamber functionally linked to the pump.

24. The device of claim 21, wherein two of the group consisting of the assay chamber, the enzyme chamber, the blood chamber, and the agonist chamber are the same chamber.

25. The device of claim 21, wherein three of the group consisting of the assay chamber, the enzyme chamber, the blood chamber, and the agonist chamber are the same chamber.

26. The device of claim 21, wherein the assay chamber, the enzyme chamber, the blood chamber, and the agonist chamber are separate chambers.

27. A system for monitoring inhibition of platelet function response comprising:

a predetermined volume of a solution of light-producing ATP-consuming enzyme;

a predetermined volume of a solution of platelet agonist;

a fluid-tight material forming an assay chamber;

a pump functionally linked to the assay chamber for pumping fluids into the assay chamber;

a light detector functionally linked to the assay chamber for detecting light emitted in the assay chamber;

a fluid-tight material forming a blood chamber for holding blood, the blood chamber functionally linked to the pump;

a fluid-tight material forming an enzyme chamber for holding a solution of a light-producing ATP-consuming enzyme, the enzyme chamber functionally linked to the pump;

a fluid-tight material forming an agonist chamber for holding a solution of a platelet agonist, the agonist chamber functionally linked to the pump;

a controller coupled to the pump and programmed to deliver to the assay chamber a predetermined volume of the blood, the predetermined volume of the light-producing enzyme solution, and the predetermined volume of the agonist solution; and a display operably coupled to the light detector for displaying results from the light detector.

28. The system of claim 27, further comprising a valve functionally linked to the pump, the assay chamber, the blood chamber, the enzyme chamber, and the agonist chamber.

29. The system of claim 27, wherein the predetermined volume of blood is less than 40 µl.

30. A device for monitoring inhibition of platelet function response comprising:

a predetermined volume of a solution of light-producing ATP-consuming enzyme;

a predetermined volume of a solution of platelet agonist;

a fluid-tight material forming an assay chamber;

a receptor adapted to hold the assay chamber;

a fluid-delivery system functionally linked to the assay chamber and configured to deliver the predetermined volume of the solution of light-producing ATP-consuming enzyme, the predetermined volume of the solution of platelet agonist, and a volume of blood into the assay chamber, wherein the fluid-delivery system comprises a pump; and a light detector functionally linked to the assay chamber for detecting light emitted in the assay chamber.

31. The device of claim 30, wherein the device further comprises an agitator functionally linked to the assay chamber to agitate fluid in the assay chamber.

32. The device of claim 31, wherein the volume of blood is in a range of 1-99 µl whole blood.

33. The device of claim 31, wherein the assay chamber has a capacity for less than 300 µl of fluid.

34. The device of claim 31, wherein the agitator comprises a movable wall of the assay chamber.

35. The device of claim 31, wherein the agitator is adapted to agitate fluid in the assay chamber by agitating the assay chamber.

36. The device of claim 31, wherein the device further includes a reagent chamber that holds the predetermined volume of the solution of platelet agonist, and wherein at least the reagent chamber and the assay chamber are formed in a disposable structure.

37. The device of claim 36, wherein the disposable structure is a disposable cuvette.

38. The device of claim 37, wherein the reagent chamber of the disposable cuvette contains the platelet agonist, the agonist is arachidonic acid, and the reagent chamber is gas tight and contains no $O_2$.

39. The device of claim 31, wherein the device further includes an enzyme chamber that holds the predetermined volume of the solution of light-producing ATP-consuming enzyme, and a reagent chamber that holds the predetermined volume of the solution of platelet agonist, and wherein at least the reagent chamber and the assay chamber are formed in a disposable structure.

40. The device of claim 30, wherein the device is adapted to be hand held.

* * * * *